United States Patent
Parramon et al.

(10) Patent No.: US 9,962,551 B2
(45) Date of Patent: *May 8, 2018

(54) MONITORING ELECTRODE VOLTAGES IN AN IMPLANTABLE MEDICAL DEVICE SYSTEM HAVING DAISY-CHAINED ELECTRODE-DRIVER INTEGRATED CIRCUITS

(71) Applicant: Boston Scientific Neuromodulation Corporation, Valencia, CA (US)

(72) Inventors: Jordi Parramon, Valencia, CA (US); Jess W. Shi, Northridge, CA (US); Emanuel Feldman, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/588,423

(22) Filed: May 5, 2017

(65) Prior Publication Data

US 2017/0232265 A1    Aug. 17, 2017

Related U.S. Application Data

(63) Continuation of application No. 15/091,938, filed on Apr. 6, 2016, now Pat. No. 9,643,016, which is a continuation of application No. 14/817,941, filed on Aug. 4, 2015, now Pat. No. 9,314,638, which is a
(Continued)

(51) Int. Cl.
*A61N 1/372* (2006.01)
*A61N 1/36* (2006.01)
(Continued)

(52) U.S. Cl.
CPC ......... *A61N 1/37241* (2013.01); *A61N 1/025* (2013.01); *A61N 1/0551* (2013.01); *A61N 1/08* (2013.01); *A61N 1/36153* (2013.01)

(58) Field of Classification Search
None
See application file for complete search history.

(56) References Cited

U.S. PATENT DOCUMENTS 4,969,465 A    11/1990  Pless et al.
5,555,888 A     9/1996  Brewer et al.
(Continued)

FOREIGN PATENT DOCUMENTS

JP    H09-114776    5/1997
WO    2005/061044   7/2005
(Continued)

*Primary Examiner* — Brian T Gedeon
(74) *Attorney, Agent, or Firm* — Lewis, Reese & Nesmith, PLLC

(57) ABSTRACT

Electrode voltage monitoring circuitry for an implantable neurostimulator system having a plurality of electrode-driver integrated circuits (ICs) in provided. Electrodes from either or both ICs can be chosen to provide stimulation, and one of the IC acts as the master while the other acts as the slave. Electrodes voltages on the slave IC are routed to the master IC, and thus the master IC can monitor both electrode voltages on the slave as well as electrode voltages on the master. Such voltages can be monitored for a variety of purposes, and in particular use of such voltage is disclosed for determining the resistance between electrodes and to set a compliance voltage for stimulation.

21 Claims, 18 Drawing Sheets

Related U.S. Application Data continuation of application No. 14/292,182, filed on May 30, 2014, now Pat. No. 9,095,726, which is a continuation of application No. 13/237,531, filed on Sep. 20, 2011, now Pat. No. 8,768,453.

(60) Provisional application No. 61/392,587, filed on Oct. 13, 2010.

(51) Int. Cl.
*A61N 1/05* (2006.01)
*A61N 1/08* (2006.01)
*A61N 1/02* (2006.01)

(56) References Cited

U.S. PATENT DOCUMENTS

| | | |
|---|---|---|
| 5,603,726 A | 2/1997 | Schulman et al. |
| 5,694,943 A | 12/1997 | Brewer et al. |
| 5,873,898 A | 2/1999 | Hemming et al. |
| 5,876,425 A | 3/1999 | Gord et al. |
| 5,941,906 A | 8/1999 | Barreras et al. |
| 6,516,227 B1 | 2/2003 | Meadows et al. |
| 6,525,986 B2 | 2/2003 | Prutchi et al. |
| 6,754,533 B1 | 6/2004 | Helfinstine et al. |
| 7,203,547 B1 | 4/2007 | Kroll et al. |
| 7,444,181 B2 | 10/2008 | Shi et al. |
| 7,805,189 B2 | 9/2010 | Stein et al. |
| 8,649,858 B2 | 2/2014 | Griffith et al. |
| 2002/0193834 A1 | 12/2002 | Levine |
| 2009/0132003 A1 | 5/2009 | Borgens et al. |
| 2009/0192567 A1 | 7/2009 | Armstrong et al. |
| 2009/0299201 A1 | 12/2009 | Gunderson |
| 2010/0256712 A1 | 10/2010 | Varrichio et al. |

FOREIGN PATENT DOCUMENTS

| | | |
|---|---|---|
| WO | 2006/029090 | 3/2006 |
| WO | 2006/065707 | 6/2006 |
| WO | 2007/075974 | 7/2007 |

| Time | Bus Command | Chip Select |
|---|---|---|
| During $t_D$ | Select E1 (E17) at MUX1 at ADDRr | CS_m = 0, CS_s = 1 |
| | Select IN1 at MUX1 at ADDRr | CS_m = 1, CS_s = 0 |
| | Select GND at MUX2 at ADDRs | CS_m = 1, CS_s = 0 |
| (settle) | | |
| | Read A/D at ADDRt | CS_m = 1, CS_s = 0 |

*Figure 7B*

| Time | Bus Command | Chip Select |
|---|---|---|
| During $t_D$ | Select E1 (E17) at MUX2 at ADDRs | CS_m = 0, CS_s = 1 |
| | Select E1 at MUX1 at ADDRr | CS_m = 1, CS_s = 0 |
| | Select IN2 at MUX2 at ADDRs | CS_m = 1, CS_s = 0 |
| (settle) | | |
| | Read A/D at ADDRt | CS_m = 1, CS_s = 0 |

*Figure 8B*

| Time | Bus Command | Chip Select |
|---|---|---|
| During $t_D$ | Select E16 (E32) at MUX1 at ADDRr | CS_m = 0, CS_s = 1 |
| | Select E1 (E17) at MUX 2 at ADDRs | CS_m = 0, CS_s = 1 |
| | Select IN1 at at MUX1 at ADDRr | CS_m = 1, CS_s = 0 |
| | Select IN2 at MUX2 at ADDRs | CS_m = 1, CS_s = 0 |
| (settle) | | |
| | Read A/D at ADDRt | CS_m = 1, CS_s = 0 |

*Figure 9C*

MONITORING ELECTRODE VOLTAGES IN AN IMPLANTABLE MEDICAL DEVICE SYSTEM HAVING DAISY-CHAINED ELECTRODE-DRIVER INTEGRATED CIRCUITS

CROSS-REFERENCE TO RELATED APPLICATIONS

This application is a continuation of U.S. patent application Ser. No. 15/091,938, filed Apr. 6, 2016 (now U.S. Pat. No. 9,643,016), which is a continuation of U.S. patent application Ser. No. 14/817,941, filed Aug. 4, 2015 (now U.S. Pat. No. 9,314,638), which is a continuation of U.S. patent application Ser. No. 14/292,182, filed May 30, 2014 (now U.S. Pat. No. 9,095,726), which is a continuation of U.S. patent application Ser. No. 13/237,531, filed Sep. 20, 2011 (now U.S. Pat. No. 8,768,453), which is a non-provisional application of U.S. Patent Application Ser. No. 61/392,587, filed Oct. 13, 2010. Priority is claimed to these applications, and they are incorporated herein by reference in their entireties.

This application is also related to U.S. Patent Application Ser. Nos. 61/392,594 and 61/392,600, both filed Oct. 13, 2010, which are both incorporated herein by reference their entireties.

FIELD OF THE INVENTION

The present invention relates generally to implantable medical devices, and more particularly to improved architectures for an implantable neurostimulator utilizing a plurality of electrode-driver integrated circuits.

BACKGROUND

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable neurostimulator.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 includes one or more electrode arrays (two such arrays 102 and 104 are shown), each containing several electrodes 106. The electrodes 106 are carried on a flexible body 108, which also houses the individual electrode leads 112 and 114 coupled to each electrode. In the illustrated embodiment, there are eight electrodes on array 102, labeled $E_1$-$E_8$, and eight electrodes on array 104, labeled $E_9$-$E_{16}$, although the number of arrays and electrodes is application specific and therefore can vary. The arrays 102, 104 couple to the IPG 100 using lead connectors 38a and 38b, which are fixed in a non-conductive header material 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils (more generally, antennas) are generally present in the IPG 100: a telemetry coil 13 used to transmit/receive data to/from an external controller 12; and a charging coil 18 for charging or recharging the IPG's battery 26 using an external charger 50. The telemetry coil 13 is typically mounted within the header 36 of the IPG 100 as shown, and may be wrapped around a ferrite core 13'.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil (antenna) 17.

The external charger 50, also typically a hand-held device, is used to wirelessly convey power to the IPG 100, which power can be used to recharge the IPG's battery 26. The transfer of power from the external charger 50 is enabled by a coil (antenna) 17'. The external charger 50 is depicted as having a similar construction to the external controller 12, but in reality they will differ in accordance with their functionalities as one skilled in the art will appreciate.

Wireless data telemetry and power transfer between the external devices 12 and 50 and the IPG 100 takes place via inductive coupling, and specifically magnetic inductive coupling. To implement such functionality, both the IPG 100 and the external devices 12 and 50 have coils which act together as a pair. In case of the external controller 12, the relevant pair of coils comprises coil 17 from the controller and coil 13 from the IPG 100. In case of the external charger 50, the relevant pair of coils comprises coil 17' from the charger and coil 18 from the IPG 100. As is well known, inductive transmission of data or power can occur transcutaneously, i.e., through the patient's tissue 25, making it particularly useful in a medical implantable device system. During the transmission of data or power, the coils 17 and 13, or 17' and 18, preferably lie in planes that are parallel, along collinear axes, and with the coils as close as possible to each other. Such an orientation between the coils 17 and 13 will generally improve the coupling between them, but deviation from ideal orientations can still result in suitably reliable data or power transfer.

U.S. Patent Application Publication 2008/0319497 ("the '497 application"), owned by the present assignee and which is incorporated herein by reference in its entirety, discloses an improved architecture 150 for an IPG 100, which is shown in FIGS. 3A-3C. Because of its pertinence to the present disclosure, some time is spent discussing pertinent aspects of the '497 application's architecture.

The improved IPG architecture 150 of FIG. 3A involves integration of various IPG functional circuit blocks on a single integrated circuit (IC) 200 via a bus 190 governed by a communication protocol, discussed further below. The centralized bus 190 is a parallel bus containing a plurality of multiplexed address and data lines operating in parallel. However, this is not strictly necessary, and instead bus 190 can comprise a serial bus as well. To communicate with the bus 190 and to adhere to the protocol, each circuit block includes bus interface circuitry 215 adherent with that protocol. Because each circuit block complies with the protocol, any given circuit block can easily be modified or upgraded without affecting the design of the other blocks, facilitating debugging and upgrading of the IPG circuitry. Moreover, because the centralized bus 190 can be taken off the integrated circuit, extra circuitry can easily be added off chip to modify or add functionality to the IPG, a point discussed further below.

Each of the circuit blocks performs standard functions in an IPG. For example, telemetry block 62 couples to the IPG telemetry coil 13, and includes transceiver circuitry for communicating with the external controller 12 (FIG. 2). The charging/protection block 64 couples to the IPG charging coil 18, and contains circuitry for rectifying power received from the external charger 50 (FIG. 2), and for charging the power source (battery) 26 in a controlled fashion. Stimulation circuit block 175 is coupled to the electrodes E1-E16 and includes circuitry for setting the program (magnitude, and polarity) for the stimulation pulses appearing at those electrodes. Block 175 also includes the drivers for the electrodes, with a Digital-to-Analog Converter (DAC) 82 being responsive to the stimulation program to supply the specified electrodes currents. Notice that the electrodes E1-E16 are connected to off-chip decoupling capacitors C1-CN prior to connection to the corresponding electrodes 106 on the leads 102 and 104 (FIG. 1A); such decoupling capacitors C1-CN prevents direct DC current injection from the IPG into the patient, which is advisable for safety, but otherwise such decoupling capacitors don't effect stimulation performance. EPROM block 177 caches any relevant data in the system (such as log data), and additional memory 66 can also be provided off-chip via a serial interface block 167. Analog-to-Digital (A/D) block 74 digitizes various analog signals for interpretation by the IPG 100, such as the battery voltage Vbat or voltages appearing at the electrodes, and is coupled to an analog bus 192 containing such voltages. Interrupt controller block 173 receives various interrupts from other circuit blocks, which because of their immediate importance are received independent of the bus 190 and its communication protocol. Note that because it handles both analog and digital signals, IC 200 comprises a mixed mode chip.

Stimulation circuit block 175 is coupled to the electrodes E1-E16 and includes circuitry for setting the program (magnitude, and polarity) for the stimulation pulses appearing at those electrodes. Block 175 also includes the drivers for the electrodes, with a Digital-to-Analog Converter (DAC) 82 being responsive to the stimulation program to supply the specified electrodes currents. Notice that the electrodes E1-E16 are connected to off-chip decoupling capacitors C1-CN prior to connection to the corresponding electrodes 106 on the leads 102 and 104 (FIG. 1A); such decoupling capacitors C1-CN prevent direct DC current injection from the IPG into the patient, which is advisable for safety, but otherwise such decoupling capacitors don't significantly affect stimulation performance.

Internal controller 160 acts as the master controller for all other circuit blocks. Specifically, each of the other circuit blocks contains set-up and status registers (not shown). The set-up registers are written to by the controller 160 upon initialization to configure and enable each block. Each circuit block can then write pertinent data at its status register, which can in turn be read by the controller 160 as necessary. Aside from such control imposed by the master controller 160, the circuit blocks outside of the controller 160 can employ simple state machines to manage their operation, which state machines are enabled and modified via the set-up registers.

As can be seen in FIG. 3A, the IC 200 contains several external terminals 202 (e.g., pins, bond pads, solder bumps, etc.), such as those necessary to connect the power source 26, to connect the coils 18, 13, to connect the external memory 66, and to connect the stimulation electrodes. Other external terminals 202 are dedicated to the various signals that comprise the centralized bus 190 to allow this bus to communicate with other devices outside of the IC 200.

The various signals comprising the bus 190 can be seen in FIG. 3B, which also discloses the protocol for communications on the bus. As shown, the centralized bus 190 comprises a clock signal (CLK) for synchronization, time-multiplexed address and data signals (A/Dx); an address latch enable signal (ALE); an active-low write enable signal (*W/E), and an active-low read enable signal (*R/E). The frequency for the clock signal, CLK, can be in the range of 32 kHz to 1 MHz, which is generally slow for a computerized protocol, but is suitably fast for operation of the IPG, which typically provides stimulation pulses on the order of tens of microseconds to milliseconds. As shown, the protocol uses a fairly simple address-before-data scheme in which an address is followed by pertinent data for that address. To discern between address and data, the address latch enable signal (ALE) is active only upon the issuance of an address, which allows the address to be latched upon the falling edge of the clock. Whether the data corresponding to a particular address is to be written or read on the next falling clock edge depends on the assertion of the write and read enable signals (*W/E; *R/E).

The nature of this protocol means that all functional blocks coupled to the centralized bus 190 are designated an address, or more likely, a range of addresses. For example, the address for a data register holding the value for the compliance voltage (in A/D block 74) might be ADDR [3401], while the address for the magnitude and duration of stimulation to be provided by electrode E6 (in stimulation circuitry block 175) may be ADDR[7655] and ADDR[7656] respectively. To assist the various functional blocks in recognizing pertinent addresses, and to ensure each block's ability to function in accordance with the centralized bus 190's protocol, each block contains bus interface circuitry 215. As this bus interface circuitry was described in detail in the above-incorporated '497 application, such details are not repeated here.

As noted in the '497 application, when the circuit blocks are coupled via the bus 190 and communicate using the protocol, it becomes a relatively simple matter to make changes to any particular block to fix circuit errors, and/or to upgrade the IC 200 for use in next-generation IPGs. Additionally, because the bus 190 is provided outside of the IC 200, it is easy to modify or add functionality to the IPG 100 outside of the IC 200. For example, and as shown in FIG. 3C, more memory 300 (preferably, nonvolatile memory) can be added. Or, systemic control can be added outside of the IC 200, for example, via an external microcontroller 240. Should an external microcontroller 240 be used in conjunction with the IC 200, the '497 application discusses manners in which control is arbitrated between the microcontroller 204 and the internal controller 160 in the IC 200. Again, such details are not repeated here.

In another off-chip extension of the architecture noted in the '497 application, and as particularly pertinent to the present disclosure, another IC 200' can be added which is similarly constructed to the first IC 200. This allows the IPG 100 in which the IC 200 and 200' are placed to provide 32 stimulation electrodes, i.e., 16 each from both of the ICs. In other words, the capacity of the IPG can be increased by "daisy chaining" a plurality of stimulation ICs together. In such an embodiment, the internal controller 160 in one of the ICs 200 or 200' can be inactivated so only one controller 160 acts as the master controller for the system.

Practical concerns arising from the use of electrode drivers in two different ICs 200 are addressed in this disclosure.

BRIEF DESCRIPTION OF THE DRAWINGS

FIGS. 7A and 7B illustrate sample and hold circuitry in the master and slave ICs, and illustrates bus commands for monitoring a voltage at an electrode at the slave IC using the sample and hold circuitry at the master IC.

FIGS. 8A and 8B illustrate sample and hold circuitry in the master and slave ICs, and illustrates bus commands for monitoring a resistance between an electrodes at the slave IC and an electrode at the master IC using the sample and hold circuitry at the master IC.

FIGS. 9A-9C illustrate sample and hold circuitry in the master and slave ICs, and illustrates bus commands for monitoring a resistance between two electrodes at the slave IC using the sample and hold circuitry at the master IC.

DETAILED DESCRIPTION

Figure 4A:
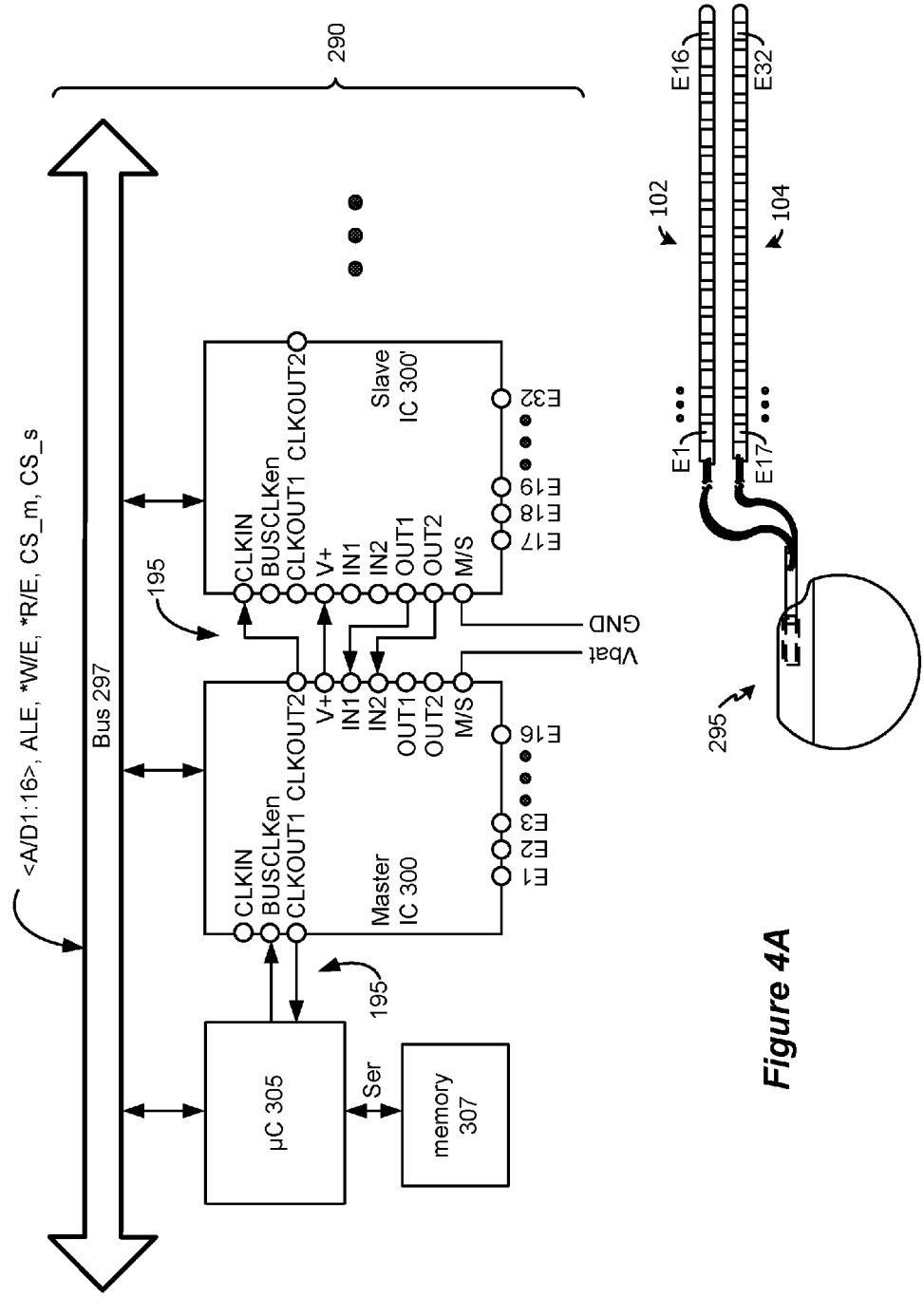
FIGS. 4A-4C illustrate aspects of an improved architecture for an IPG utilizing a plurality of electrode-driver ICs.

FIG. 4A shows an improved system 290 for an IPG 295 having an improved architecture in which two electrode driver ICs 300 and 300' are daisy chained to double the electrode capacity in the IPG, i.e., from 16 to 32 electrodes as shown. (The metallic case 30 of the IPG 295 can also comprise an electrode, but this is not shown for simplicity).

Figure 3A:
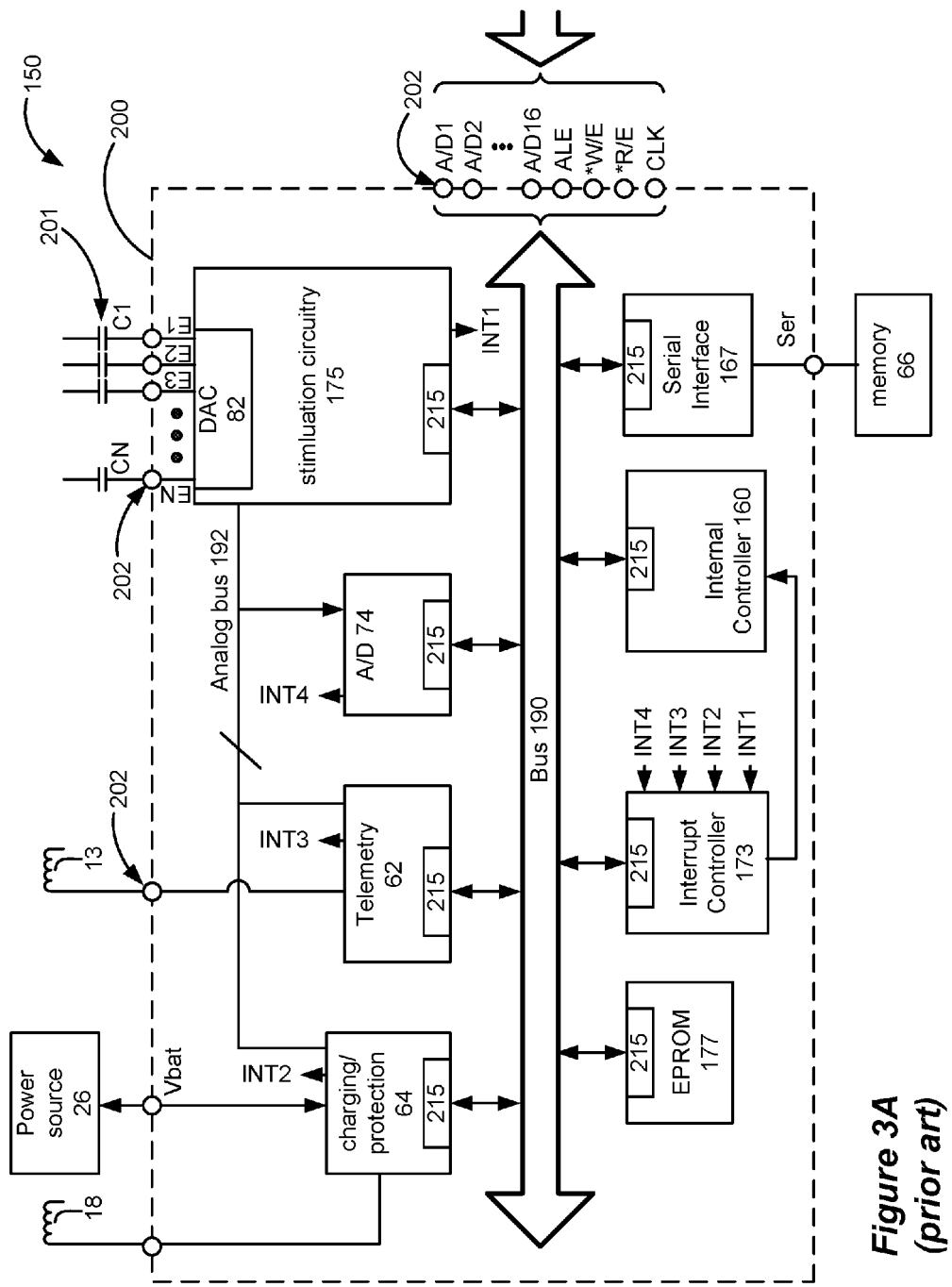
FIGS. 3A-3C illustrate aspects of an IPG architecture using a centralized bus, as disclosed in U.S. Patent Application Publication 2008/0319497.
Figure 3B:
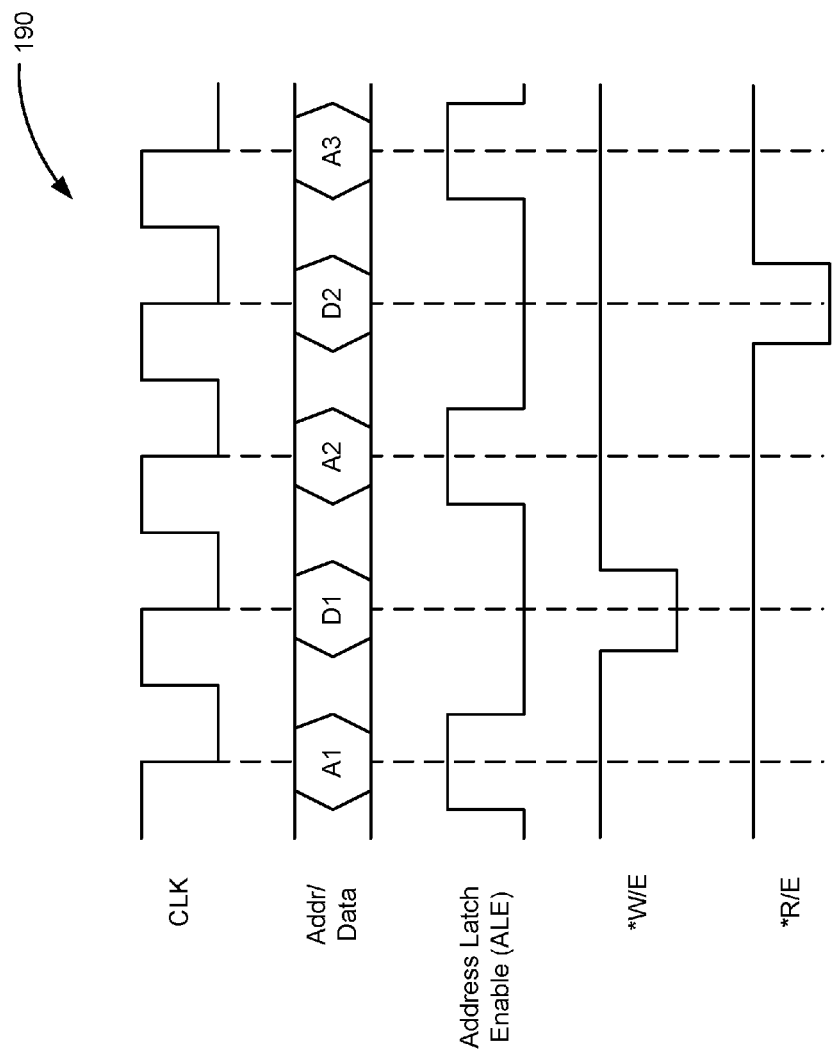
Figure 3C:
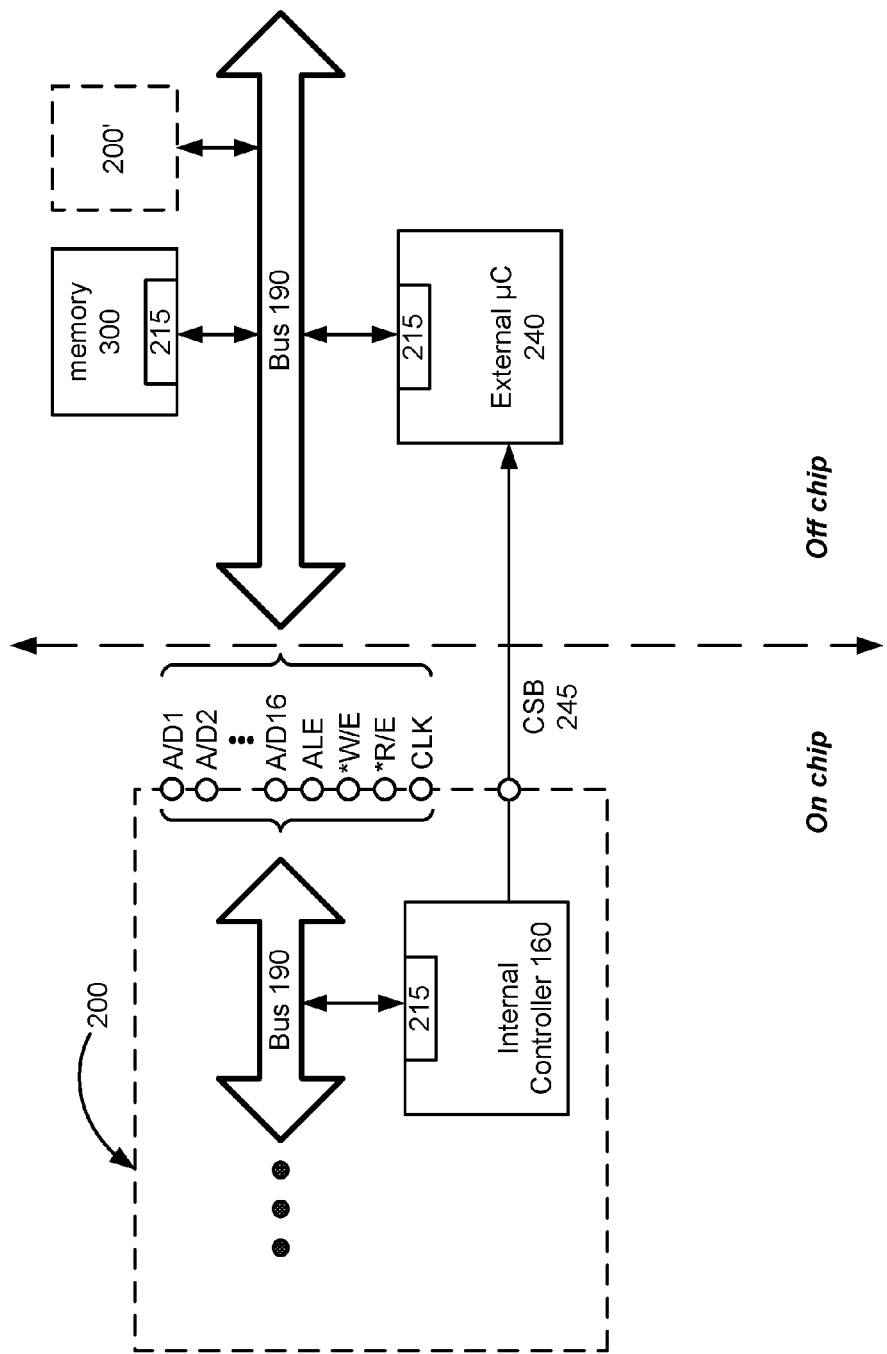

In this example, one of the ICs 300 acts as a master, while the other 300' acts as a slave, as will be explained in further detail below. Both ICs 300 and 300' are connected to a bus 297, which is similar to the bus described in the Background, but which includes additional control signals for selecting either of the two chips: CS_m, which comprises a chip select for the master 300, and CS_s, which comprises a chip select for the slave 300'. Note that while the clock signal (CLK; FIG. 3B) remains important in the communication protocol, it is not included as one of the bus signals shared by all ICs in the system; clocking circuitry in the system 290 is discussed further with reference to FIG. 10 below.

Figure 1:
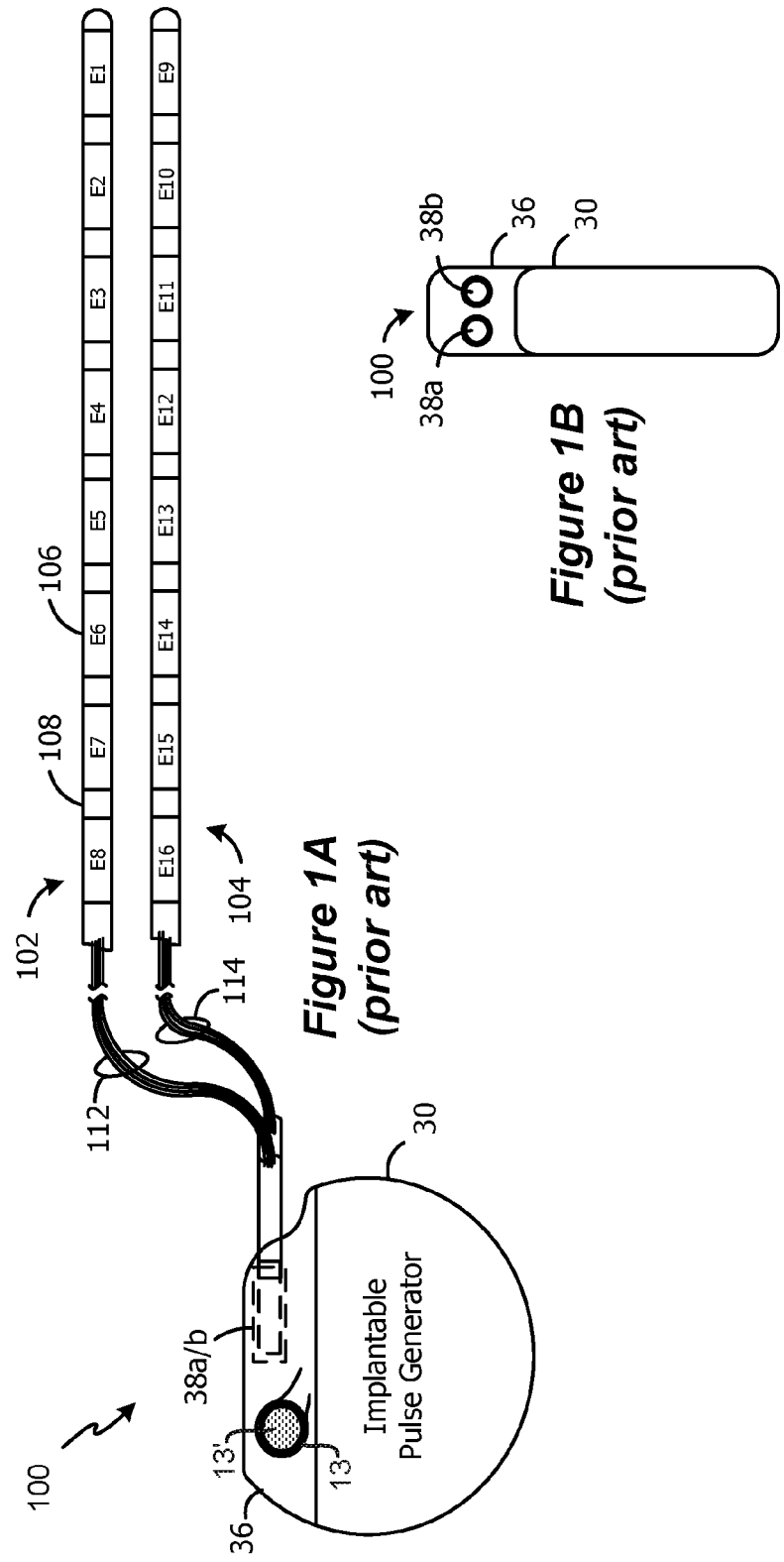
FIGS. 1A and 1B show an implantable pulse generator (IPG), and the manner in which an electrode array is coupled to the IPG in accordance with the prior art.
Figure 2:
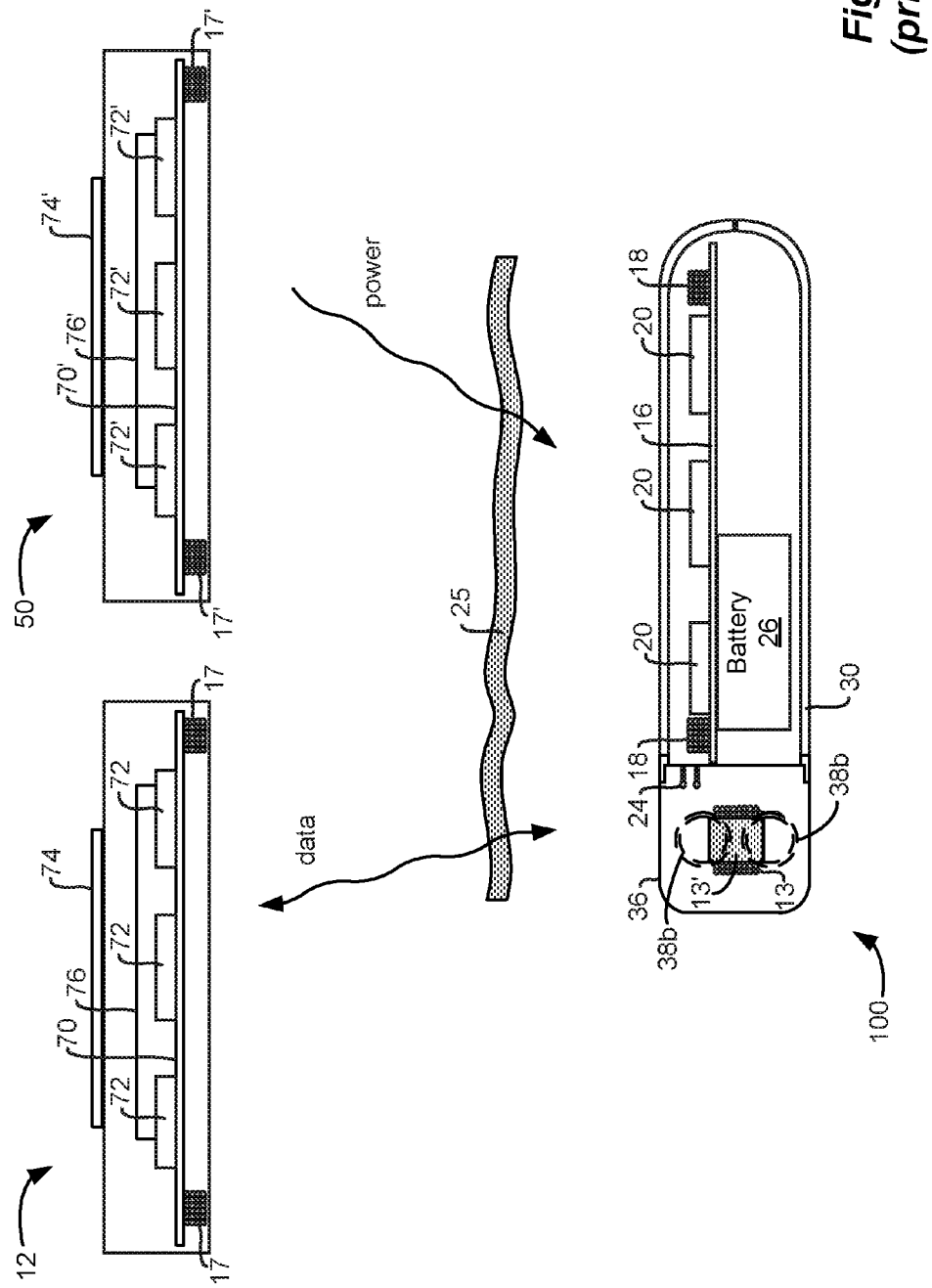
FIG. 2 illustrates an IPG, an external controller, and an external charger in accordance with the prior art.

Also connected to the bus is a microcontroller 305, which provides for control of functions in the system 290 not handled by various circuit blocks in the ICs 300 and 300', and otherwise generally acts as the system's master. For example, bus communications are ultimately controlled by the microcontroller 305, which controls the issuance of clocks needed for the communication protocol as explained further below, and which also issues the bus control signals (e.g., ALE, W/E*, R/E* in FIG. 3B). In another example, microcontroller 305 schedules when the IPG 295 is to listen for telemetry from the external controller 12 (FIG. 2). See, e.g., U.S. Pat. No. 7,725,194, discussing this issue in further detail. Microcontroller 305 also connects to a memory (Flash EPROM) chip 307 in the system 290, which can hold the operating software for the system, and which can also act as a free space to log data in the system, e.g., data to be reported to the external controller 12 for analysis and/or feedback to the patient.

In the embodiment shown, each of the ICs 300 and 300', which will be explained in detail shortly, are fabricated identically, even though they are destined to act as master or slave in the system. Fabricating only a single electrode-driver IC is a great convenience, as the manufacturer does not have to different fabricate, track, and test, separate master and slave ICs for the system 290. Whether any given IC operates as a master or slave in the system depends on how it is connected to the remainder of the system 297, i.e., such chips are bond programmable. As shown in FIG. 4A, each IC has an input, M/S, which when provided a voltage informs the IC that it is the master 300, and when not informs the IC that it is a slave 300'. This can be accomplished by connecting the M/S input to a particular node on the IPG's PCB, such as Vbat, the battery 26 voltage (FIG. 2), in the case of the master 300, or ground (GND) in the case of the slave 300'. When a given IC understands that it is operating as a slave, it deactivates certain of its circuit blocks, as will be explained later.

Also shown in FIG. 4A are certain off-bus signals 195. These signals and their functions will be discussed in more detail later.

Figure 4B:
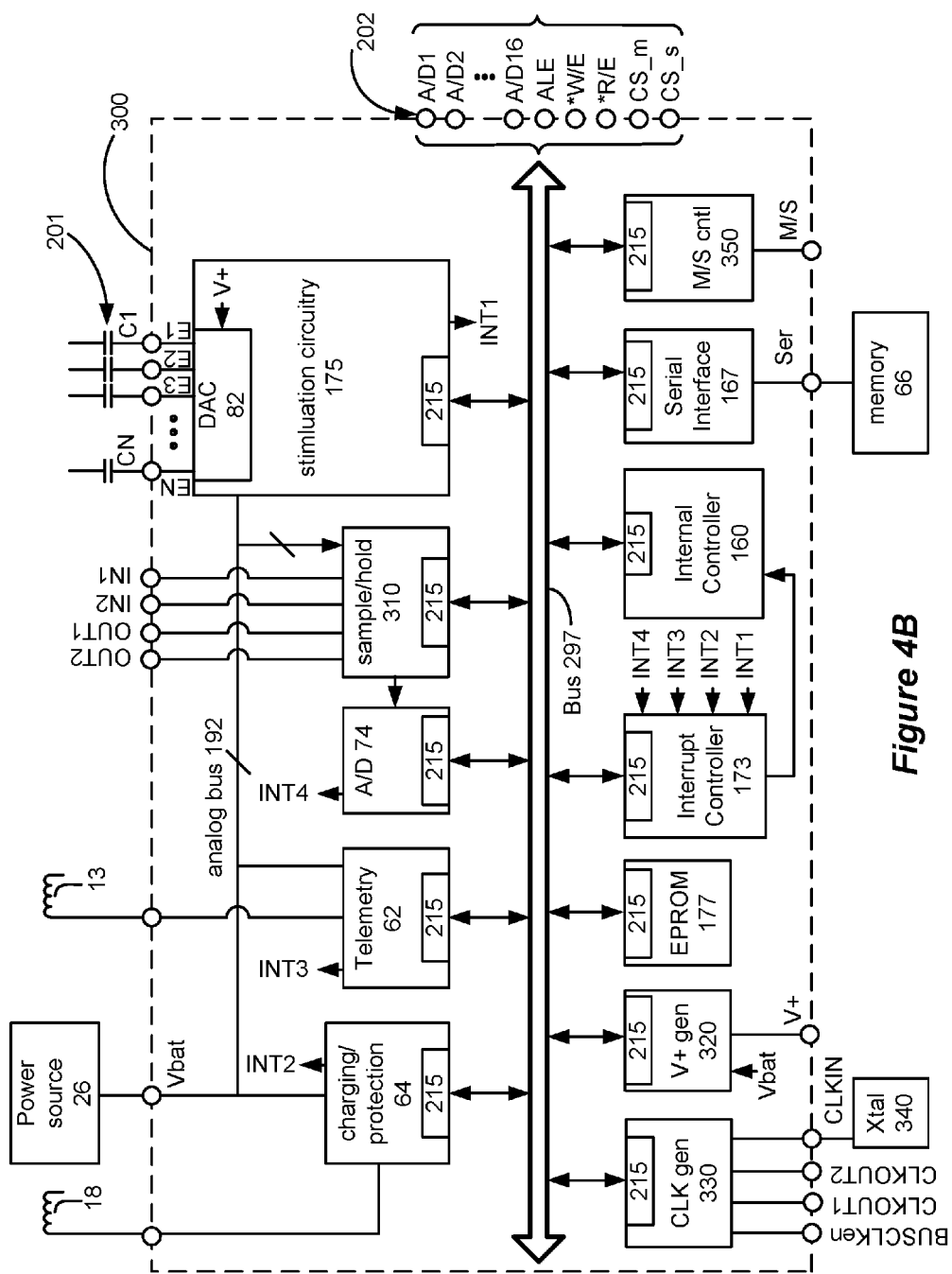

FIG. 4B shows the circuit blocks in either of the identical master 300 or slave 300' ICs. Many of these circuit blocks were discussed earlier in conjunction with the Background (see FIG. 3A), and so discussion of those blocks is not repeated here. Of particular note and new to FIG. 4B are the sample and hold block 310, the compliance voltage (V+) generator block 320, the clock generator block 330, and a master/slave (M/S) controller 350. As with other circuit blocks on the IC, these circuit blocks contain interface circuitry 215 to allow them to communicate on, and be controlled by, the bus 297 in accordance with the protocol discussed earlier.

Sample and hold circuitry block 310 will be explained in detail later, but for now merely note that it contains circuitry for sampling and holding various analog voltages comprising the analog bus 192, including the electrode voltages. Once sample and hold block 310 has operated to resolve a particular voltage, it can be sent to the A/D block 74, where it is digitized and disseminated via the communication bus 297 to wherever in the system 290 it is needed for analysis. Signals IN1, IN2, OUT1 and OUT2 are used to route various analog signals between the two ICs 300 and 300', as explained later.

V+ generator block 320 generates a compliance voltage, V+, which is used by the current sources (DAC 82) in the stimulation circuitry block 175. It does so by voltage boosting the battery voltage, Vbat, to an appropriate V+ voltage used to power the current sources to an optimal level, which optimal level can be deduced in part by monitoring the electrode voltages during stimulation. See, e.g., U.S. Pat. Nos. 7,872,884; 7,444,181; 7,539,538, for further details concerning the generation of compliance voltage V+ in an IPG.

Clock generator 330 generates the communications clocks used by the communications protocol on the bus 297. As noted earlier though, a clocking signal does not comprise part of the communication bus 297. Operation of the clock generator 330 will be explained in detail with respect to FIG. 10.

Figure 4C:
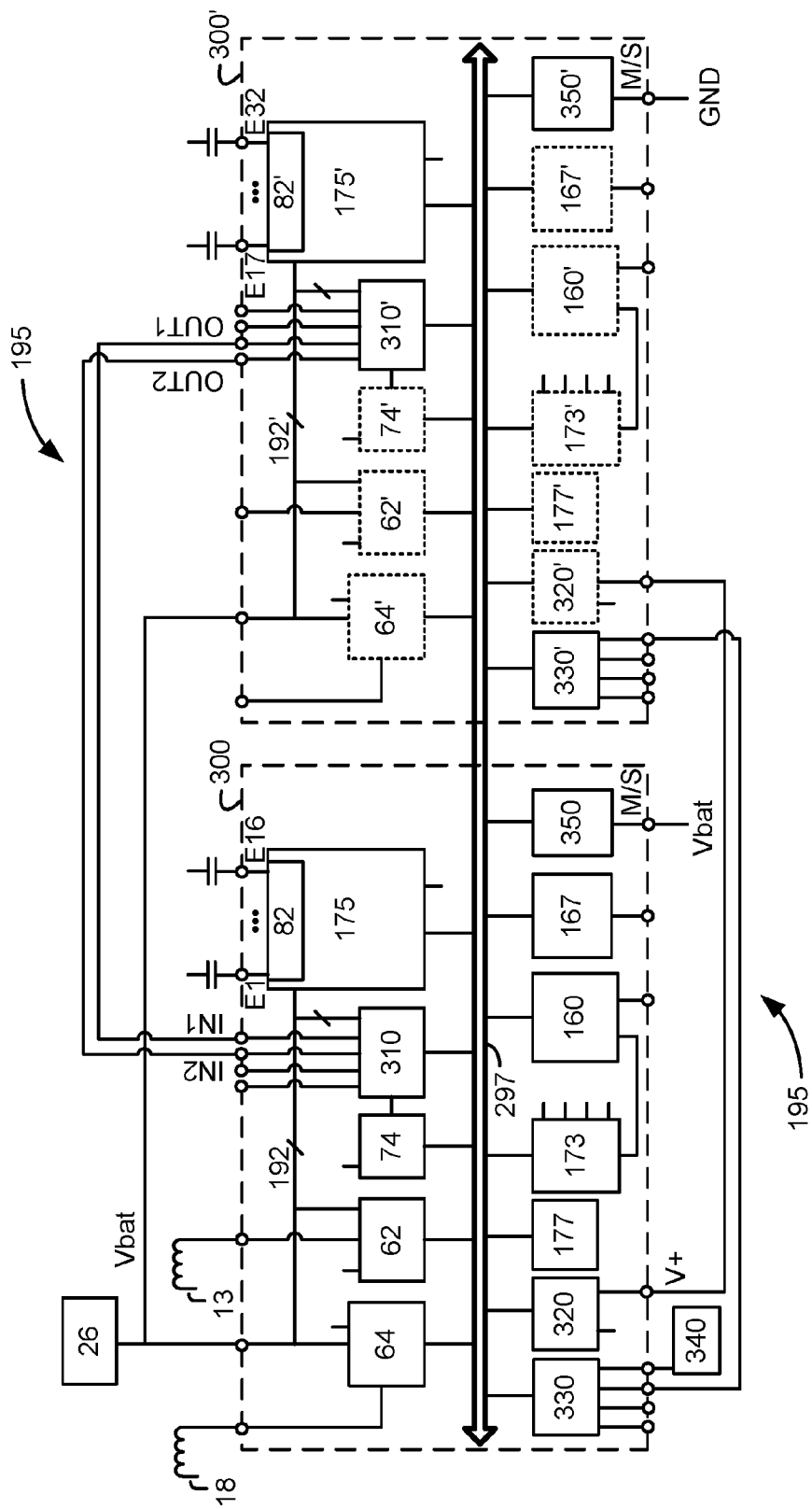

Master/slave controller 350 receives the M/S input mentioned earlier, and interprets that input to inform the IC whether it is operating and a slave or master, and this is illustrated further in FIG. 4C. In FIG. 4C, the master and slave 300 and 300' are shown as connected, including bus-based 297 and off-bus 195 connections. Note that corresponding circuit blocks in the slave IC 300' are denoted by a prime symbol. As described earlier, the M/S inputs to the master/slave controllers 350 differ (high; low) depending on which IC is acting as the master or slave. In the slave IC 300' the master/slave controller 350' interprets the grounded input, and informs certain other circuit blocks that they are to be disabled in favor of use of those same circuit blocks in the master IC 300. Specifically, the charging/protection block 64', telemetry block 62' A/D block 74', V+ generator 320', interrupt controller 173', and the internal controller 160' are all disabled in the slave IC 300', and are shown in dotted lines to illustrate that fact. Disabling of each of these circuit blocks can occur in accordance with the state machines operating at each block upon receipt of information from the master/slave controller 350, and such disabling can be effected by disabling the bus drivers and bus receivers operating in the interface circuitry in the affected blocks (see the above-incorporated '497 application). Still operative in the slave IC 300' however are the stimulation circuitry block 175' coupled to the electrodes, the sample and hold circuit block 310', the clock generation circuitry 330', and the master/slave controller 350' itself.

With regard to the various off-chip signals 195, note that the compliance voltage, V+, generated in the master IC 300 is routed to the slave IC 300' for use in the slave's stimulation circuitry block 175'. The changing and telemetry coils 18 and 13 are only coupled to the master IC 300 where their corresponding blocks 64 and 62 are active. The battery 26 (FIG. 2) voltage, Vbat, is shared by both ICs 300 and 300' (as well as the microcontroller 305), and other components internal to the IPG 100. An external crystal oscillator 340 is coupled to the CLKIN input only on the master IC 300.

FIGS. 5-9C illustrate the operation of the sample and hold circuitry blocks 310 and 310' active in both ICs 300 and 300', and further illustrate how off-bus signal 195 carried between IN1, IN2, OUT1, and OUT2 are used in the system to monitor analog signals in both ICs. Additionally, these Figures provide examples of commands used on the bus 297 to provide the desired stimulation and monitoring functions.

Figure 5:
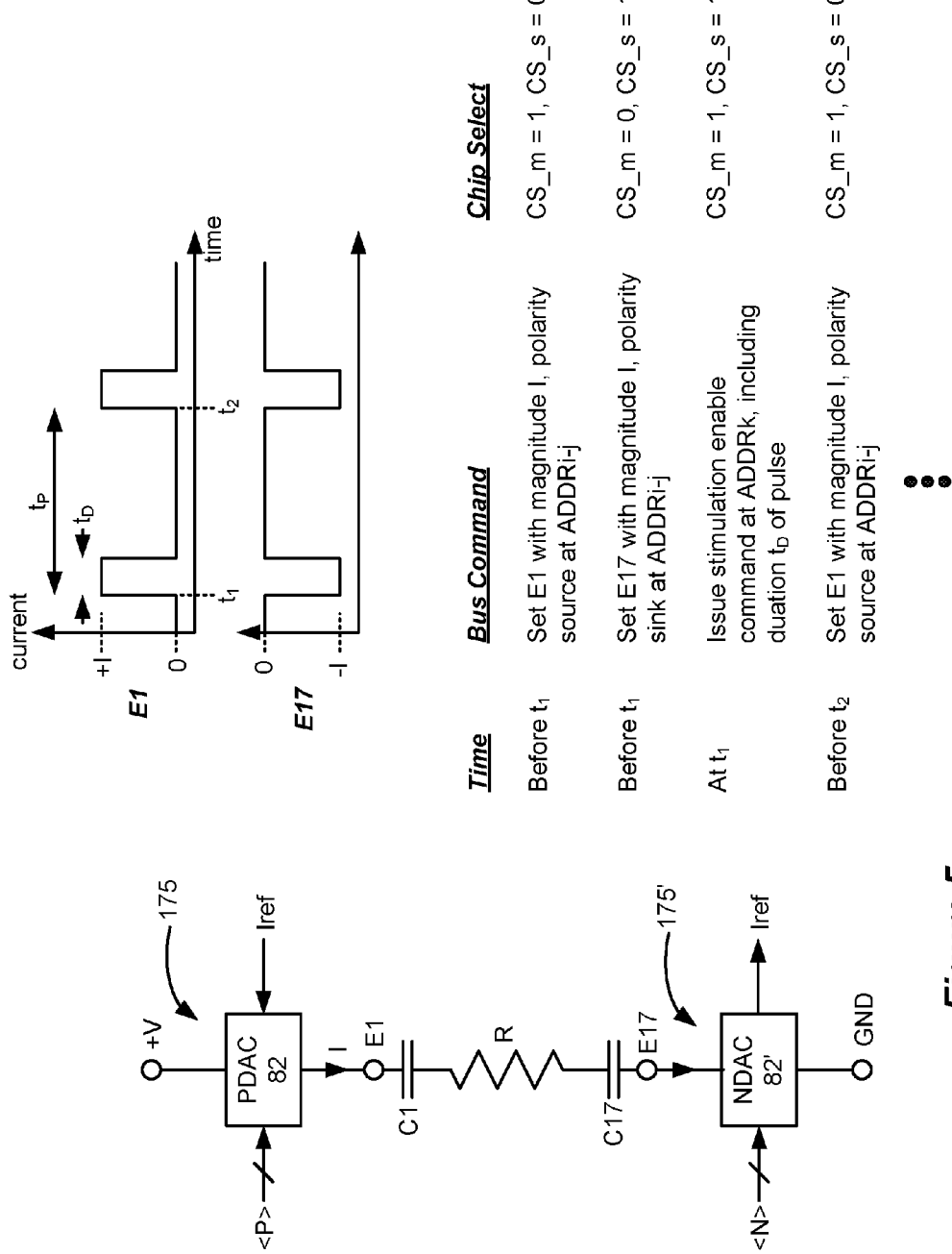
FIG. 5 illustrates circuitry, timing, and bus commands for simultaneously providing a situation pulse at electrodes on different of the electrode-driver ICss in the improved architecture.

FIG. 5 shows an example of the stimulation that can be provided by the system 290, and in particular shows the provision of a monophasic pulse train to a patient's tissue, which is represented in FIG. 5 as a resistance, R. (System 290 can similarly provide biphasic pulses as one skilled in the art understands, and as is explained in the above-incorporated concurrent application. However, monophasic pulses are illustrated for simplicity). In the example shown, electrode E1 from the master IC 300 is used as the anode which sources a current +I for a pulse duration of $t_D$, and electrode E17 from the slave IC 300 is used as the cathode for the sink of that current (−I). The pulses at both electrodes have a periodicity of $t_P$.

The currents (+I, −I) appearing at each electrode are set by Digital-to-Analog Converters, or DACs 82, which comprises part of the stimulation circuitry 175. As is known, the DACs 82 provide the desired current based on digital control signals (<P>, <N>), which control signals specify the amount that a reference current, Iref, is to be amplified. A DAC used as the anodic source is called a PDAC, while a DAC used as the cathodic sink is called a NDAC. See, e.g., U.S. Patent Application Publication 2007/0038250, for further details concerning the specifics of PDAC and NDAC circuitry useable in a system such as system 290. Because electrodes E1 and E17 in this example are respectively driven by the master and slave ICs 300 and 300', the stimulation circuitry 175 and 175' and DACs 82 and 82' at each are implicated in providing the desired pulses.

Prior to the delivery of the desired pulses, the stimulation circuitry 175 in each of the ICs is loaded with the appropriate stimulation parameters. These parameters (magnitude and polarity of current) are communicated via bus 297 from the microcontroller 305 based upon the therapy program that has been established for the patient, which therapy program can be changed from time to time by the external controller 12 (FIG. 2). As noted earlier, the bus-based communication protocol allows for these parameters to be sent to various addresses designated for the various circuit blocks. For example, the magnitude for the current at electrode E1 may be stored at ADDRi in the stimulation circuitry 175, while the polarity is stored at ADDRj. These parameters can be loaded serially for each electrode, and in advance of the issuance of the pulse. Thus, and referring to the command table in FIG. 5, it is seen that these parameters are loaded for each of electrodes E1 and E17 before t1—the first pulse in the train.

When ICs 300 and 300' are daisy chained as disclosed, it is important to properly differentiate between active circuit blocks in each of the two ICs. For example, and as discussed earlier with respect to FIG. 4C, the stimulation circuitry block 175', the sample and hold circuit block 310', and the clock generation circuitry 330', are active in both ICs, and share the same addresses. Differentiation between the two ICs occurs by use of the chip select signals, CS_m and CS_s. Thus, as shown in FIG. 5, although E1 and E17 are associated with the same addresses ADDRi and ADDRj, the chip select signal is used to differentiate them and to program the stimulation circuitry 175 in the appropriate ICs. Thus, the stimulation parameters for electrode E1 are written to ADDRi and j with CS_m asserted, indicating programming of the stimulation circuitry 175 in the master IC 300 (i.e., that which drives electrodes E1-E16). By contrast, the stimulation parameters for electrode E17 are written to ADDRi and j with CS_s asserted, indicating programming of the stimulation circuitry 175 in the slave IC 300' (i.e., that which drives electrode E17-E32).

It is important to synchronize therapeutic pulses occurring at electrodes in each of the ICs 300 and 300'. Thus, after the stimulation parameters have been loaded, it must be ensured that the stimulation pulses will issue from the various electrodes on the ICs 300 and 300' at the same time. For example, if the anodic pulse issues from electrode E1 issues slightly prior to the issuance of the cathodic pulse at electrode E17, charge will be injected into the patient's tissue during that slight time with no return path. Likewise, if the anodic pulse ceases from electrode E1 issues slightly prior to cessation of the cathodic pulse at electrode E17, charge will be depleted from the patient's tissue during that slight time. Such charge build up can impede therapy, or could injure the patient.

To ensure simultaneous issuance of the pulses, bus-based communication is used in system 290 to simultaneously trigger the issuance of both pulses. As shown in FIG. 5, at time t1, i.e., after the stimulation parameters for each electrode have been loaded to each of the ICs 300 and 300', a stimulation enable command is issued on the bus with both of the chip select signals asserted (i.e., CS_m=CS_s=1). This allows both of stimulation circuitries 175 and 175' to receive the stimulation enable signal at the same time, and to provide the pre-stored stimulation parameters to their DACs 82 and 82', thus producing the desired currents simultaneously. In this example, the stimulation enable command is sent to ADDRk. If not pre-loaded as a stimulation parameter, the pulse duration $t_D$ can be included with the simulation enable command.

Another important issue, and one addressed in the improved system 290, deals with monitoring various voltages in the ICs 300 and 300', such as the electrode voltages. Assessing such voltages is beneficial for many reasons. Knowing the voltages present at the electrodes during stimulation can be useful in setting the compliance voltage, V+, at the V+ generator 320 (FIG. 4B) to an appropriate and power-efficient magnitude. See, e.g., U.S. Pat. No. 7,444, 181. Also, knowing the electrode voltages allows the resistance between the electrodes, R, to be calculated, which is useful for a variety of reasons.

Figure 6:
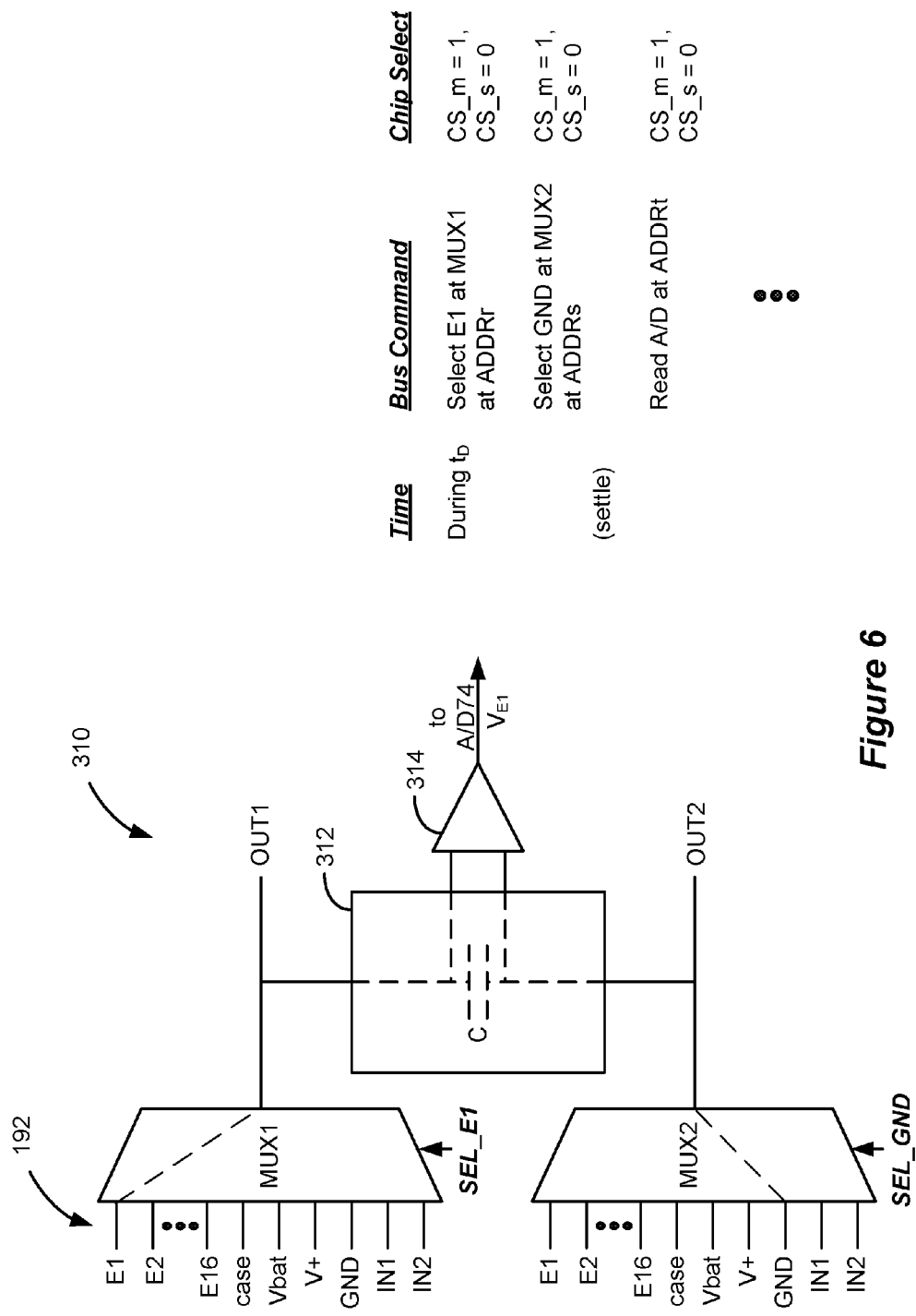
FIG. 6 illustrates sample and hold circuitry in the master IC, and illustrates bus commands for monitoring a voltage at an electrode at the master IC using the sample and hold circuitry.

Voltage monitoring in any given IC 300 is performed by the sample and hold circuitry 310, which is shown in FIG. 6. As shown, sample and hold circuitry 310 comprises two multiplexers (MUX1 ad MUX2), either of which can select from a plurality of signals comprising the analog bus 192 (FIG. 4B), such as the electrode voltages (E1-E16), the voltage on the metallic case 30, which is usually grounded, the battery voltage (Vbat), the compliance voltage (V+), or ground (GND). Each MUX receives a control signal to choose one of these various inputs. (In reality, the control signal for each MUX may comprise a plurality of digital control signals. For example, if the MUX is capable of selecting from 16 different inputs, then four control signals may be used).

FIG. 6 shows the example of measuring the voltage on electrode E1 during stimulation. MUX1 chooses this electrode via control signal(s) SEL_E1, which allows the voltage on E1 to pass to OUT1. MUX2 chooses ground (GND) as a reference (e.g., 0 Volts), which is passed to OUT2. As shown in the command table in FIG. 6, both of these selections can be made via the bus 297 at an appropriate time during the duration of the pulse (i.e., during $t_D$), where it is assumed that MUX1 is accessible via ADDRr and MUX2 via ADDRs. Because the voltage, $V_{E1}$, being monitored is already present at the master IC 300, the chip select signals are set accordingly (CS_m=1, CS_s=0). Intervening between these outputs OUT1 and OUT2 is holding circuitry 312. Holding circuitry 312 can comprise any circuitry suitable for holding and stabilizing the voltage to be measured, and as illustrated comprises a single capacitor, C. However, more sophisticated holding circuitry 312 can be used, such as the circuitry disclosed in above-incorporated concurrent application. Alternatively, and particularly when DC voltages are being monitored, holding circuitry 312 can be dispensed with altogether.

The voltages on each plate of the capacitor are sent to a differential amplifier 314, which after a settling period outputs the difference between the two, which in this case is $V_{E1}$–0 or $V_{E1}$. This analog voltage can then be sent to A/D block 74 (FIG. 4B), where it is digitized. This value can then be read (at ADDRt in A/D block 74), and used elsewhere in the system, such as the V+ generator 320 (FIG. 4B).

Figure 7A:
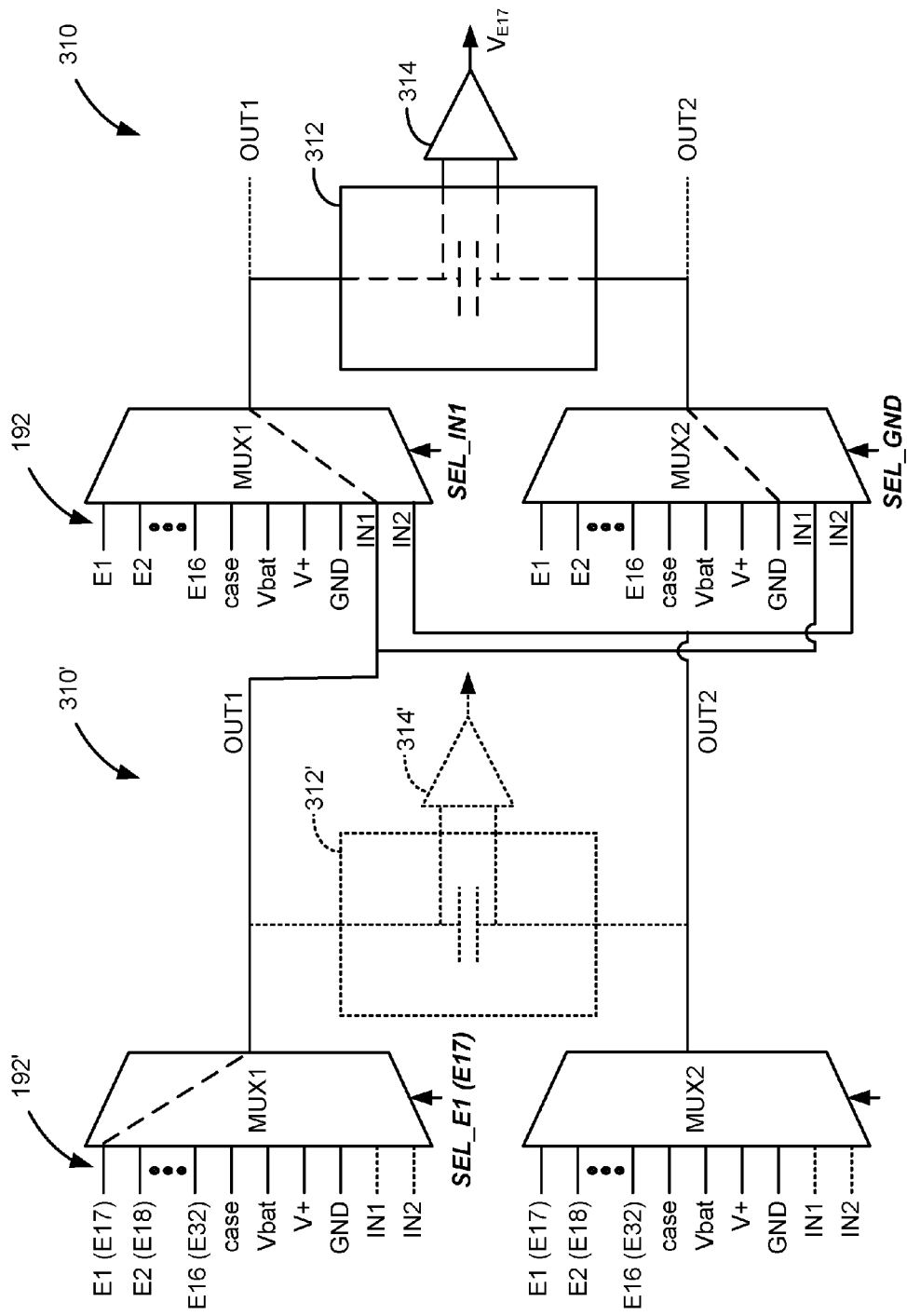

When the voltage being measured comes from the slave IC 300' instead of the master 300, the interconnection between the two sample and hold circuitries 310 and 310' is implicated, as shown in FIG. 7A. Such interconnection involves the use of off-bus signals IN1, IN2, OUT1, and OUT2, which were briefly mentioned earlier, and which are shown at a high level in FIG. 4A. As shown there, and in further detail in FIG. 7A, note that OUT1 from MUX1 on the slave IC 300' is sent to IN1 in the master IC 300, which in turn is sent as an input to both of the master IC's MUXes. OUT2 from MUX2 on the slave IC 300' is sent to IN2 in the master IC 300, which again is sent as in input to both of the master IC's MUXes. This interconnection of the sample and hold circuitries 310 and 310' operates to pull any relevant voltages to be monitored from the sample and hold circuitry 310' in the slave IC 300' to the sample and hold circuitry 310 in the master IC 300. Because the holding circuitry 312' and differential amplifier 314' are not used in the slave IC 300', they are illustrated in dotted lines in FIG. 7A. This interconnection of the sample and hold circuitries 310 and 310' also result in inputs IN1 and IN2 to the MUXes in the slave not being used, and the outputs OUT1 and OUT2 in the master not being used, which again is represented by dotted lines. Routing on the PCB between the two IC 300 and 300' establishes the proper connections between OUT1 and OUT2 from the slave IC 300', and IN1 and IN2 in the master IC 300.

FIG. 7A illustrates monitoring the voltage on electrode E17 (that is, E1 from the slave IC 300'), with the command table for doing the same provided in FIG. 7B. E17 is selected at MUX1 via its MUX address ADDRr, but with the slave IC selected (CS_s=1, CS_m=0). Because no other voltage is of interest is pulled from the slave IC, MUX2 in the slave selects no value. The output from MUX1, OUT1, is routed off chip to input IN1 on the master IC 300, where it is selected at MUX1. Again, MUX1 is addressed at ADDRr, but this time with the master selected (CS_m=1, CS_s=0), which routes the voltage on E17 to the top plate of the capacitor in sample and hold circuit 312. Because in this example it is desired to know the absolute value of the voltage on E17, MUX2 (address ADDRs) in the master selects the ground input, which routes ground to the bottom plate of the capacitor. After allowing for settling, differential amplifier 314 outputs the difference between its two inputs, $V_{E17}$, which can then be passed to A/D block 74 for interpretation as discussed before.

Figure 8A:
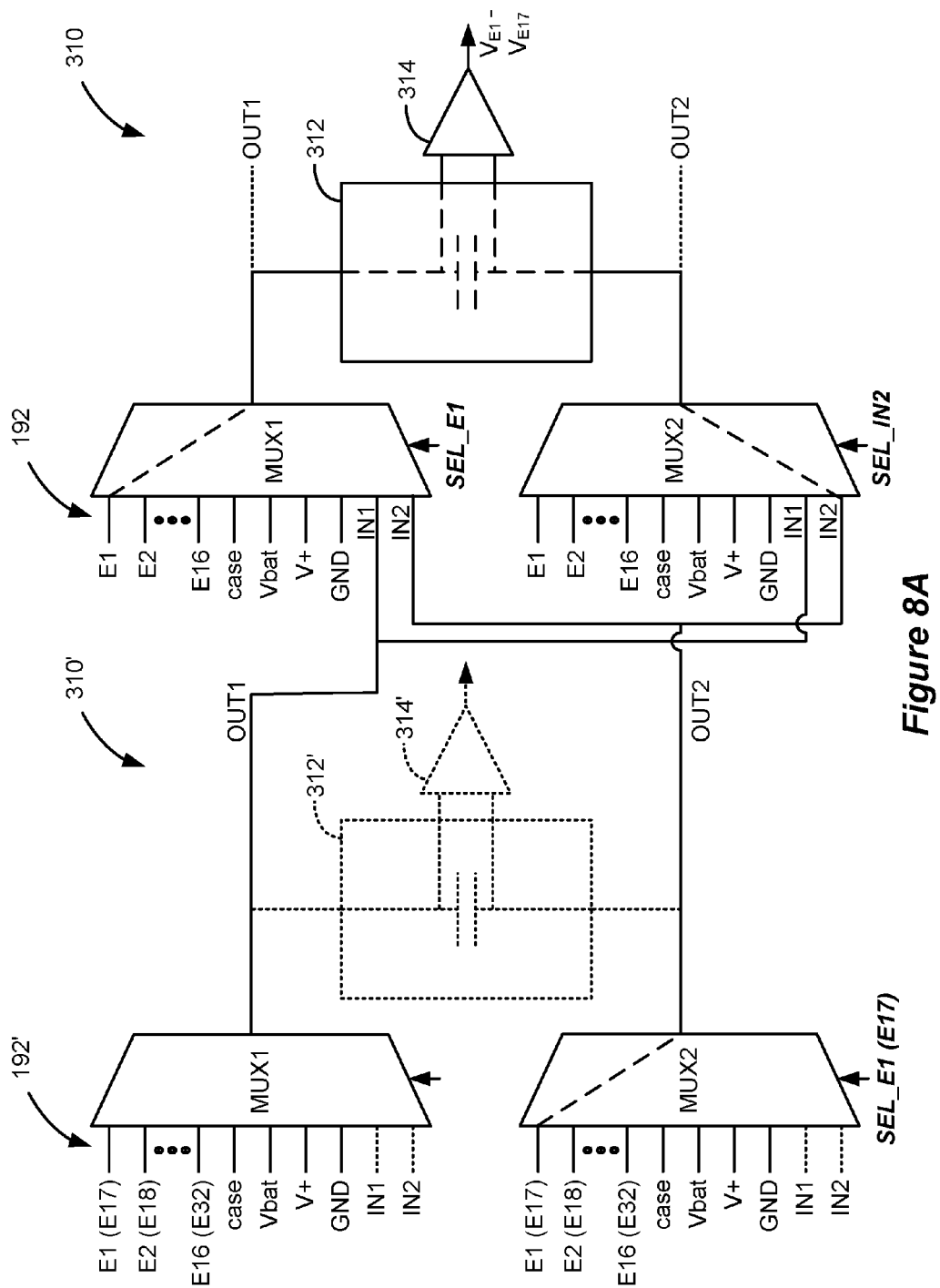

Monitoring the voltages at electrodes during stimulation is further useful in calculating the resistance between electrodes, and examples using sample and hold circuitry 310 to do so are shown in FIGS. 8A-9C. FIG. 8A and 8B continue the example of FIG. 5, but with the goal of determining the resistance R between anode electrode E1 and cathode electrode E17. Such a resistance measurement requires assessment of the voltages at both electrodes, $V_{E1}$ and $V_{E17}$. Here, only one of the voltages (E17) needs to be pulled from the slave IC 300' to the sample and hold circuit 310 in the master IC 300. Because this electrode is the cathode, MUX2 is selected at the slave (ADDRs; CS_s=1; CS_m=0) to pull this voltage to IN2 at the master IC 300. Anode electrode E1 is selected by MUX1 at the master (ADDRr; CS_m=1; CS_s=0), and IN2 (E17 as pulled from the slave IC 300') is selected by MUX2 at the master (ADDRs; CS_m=1; CS_s=0). The resulting voltage difference across the capacitor in holding circuitry 312 ($V_{E1}-V_{E17}$) is then reflected at the output of the differential amplifier 314. Because the current used to form these voltages is known (I), the resistance between the electrodes can be calculated in the IPG 295 as ($V_{E1}-V_{E17}$)/I, with perhaps some adjustment to the calculation to account for small voltage drops across the decoupling capacitor, a point discussed in further detail in the concurrent application.

Figure 9A:
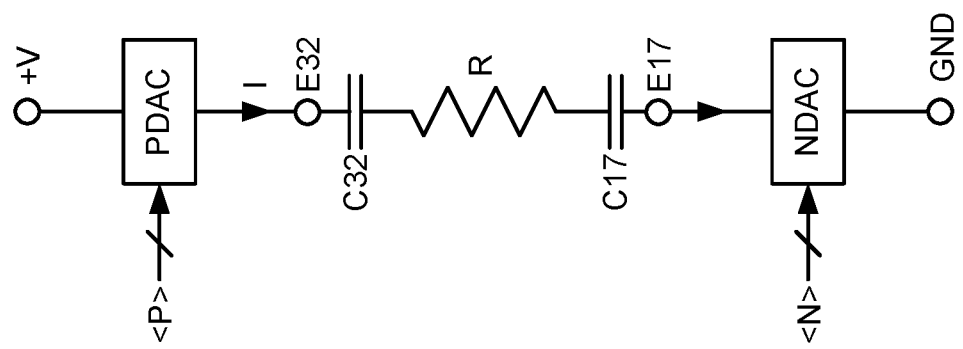
Figure 9B:
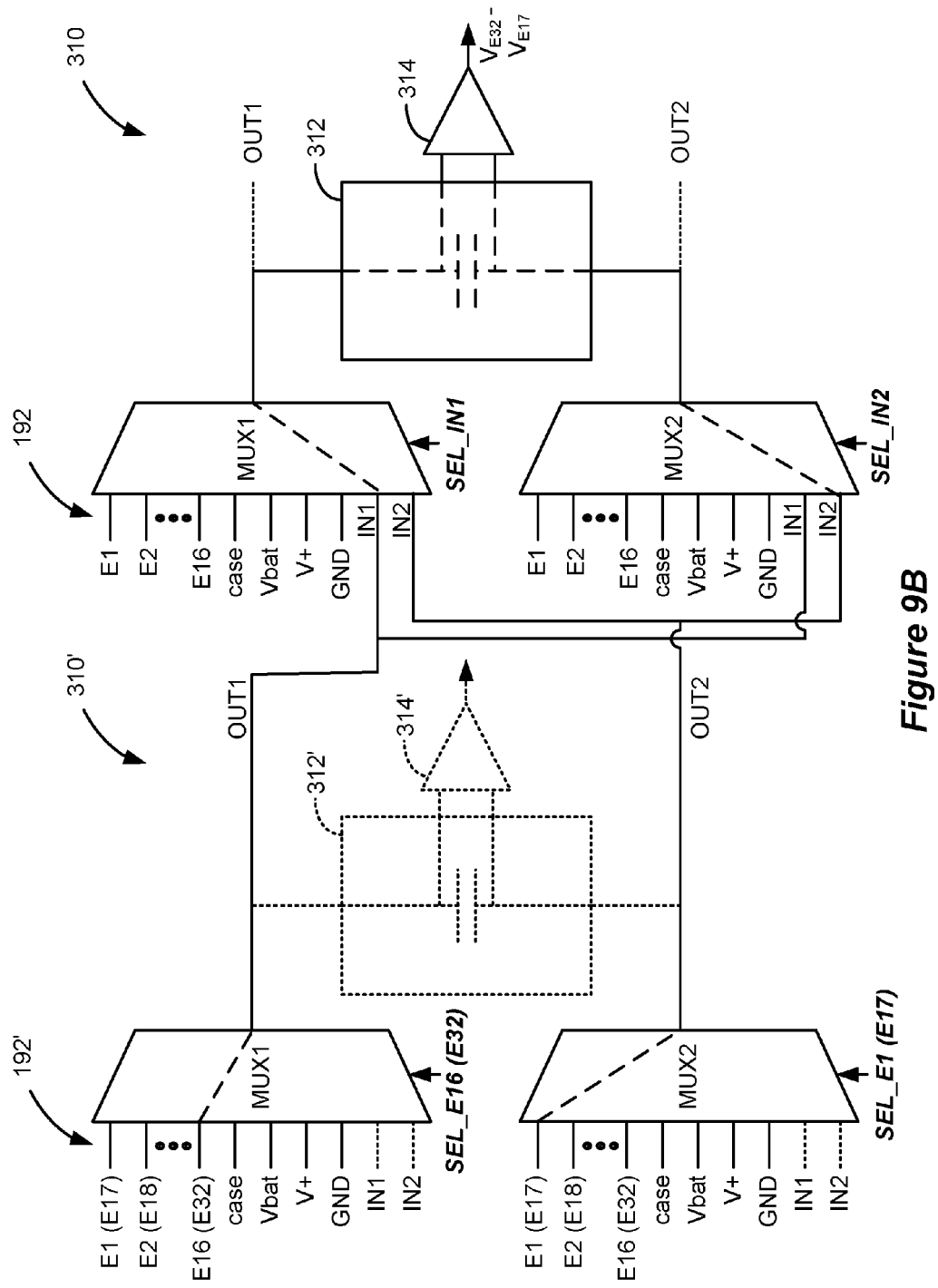

FIGS. 9A-9C illustrate a more complicated case in which the resistance between anode electrode E32 and cathode electrode E17 are measured as shown in FIG. 9A. Here, both electrodes appearing in the slave IC 300'. Because of this, and as shown in FIG. 9B, the voltages for each of these electrodes are selected by MUX1 and MUX2 respectively in the slave, which pass them to the master IC 300 at inputs IN1 and IN2 respectively. The MUXes in the master sample and hold circuit 310 then choose these inputs IN1 and IN2, placing the voltage of the anode (E32) on top of the capacitor, and the voltage of cathode E17 on the both of the capacitor in the holding circuit 314. As before, the differential amplifier 314 outputs the difference between the two ($V_{E32}-V_{E17}$), and the resistance between then can then be calculated using the known current, I.

Figure 10:
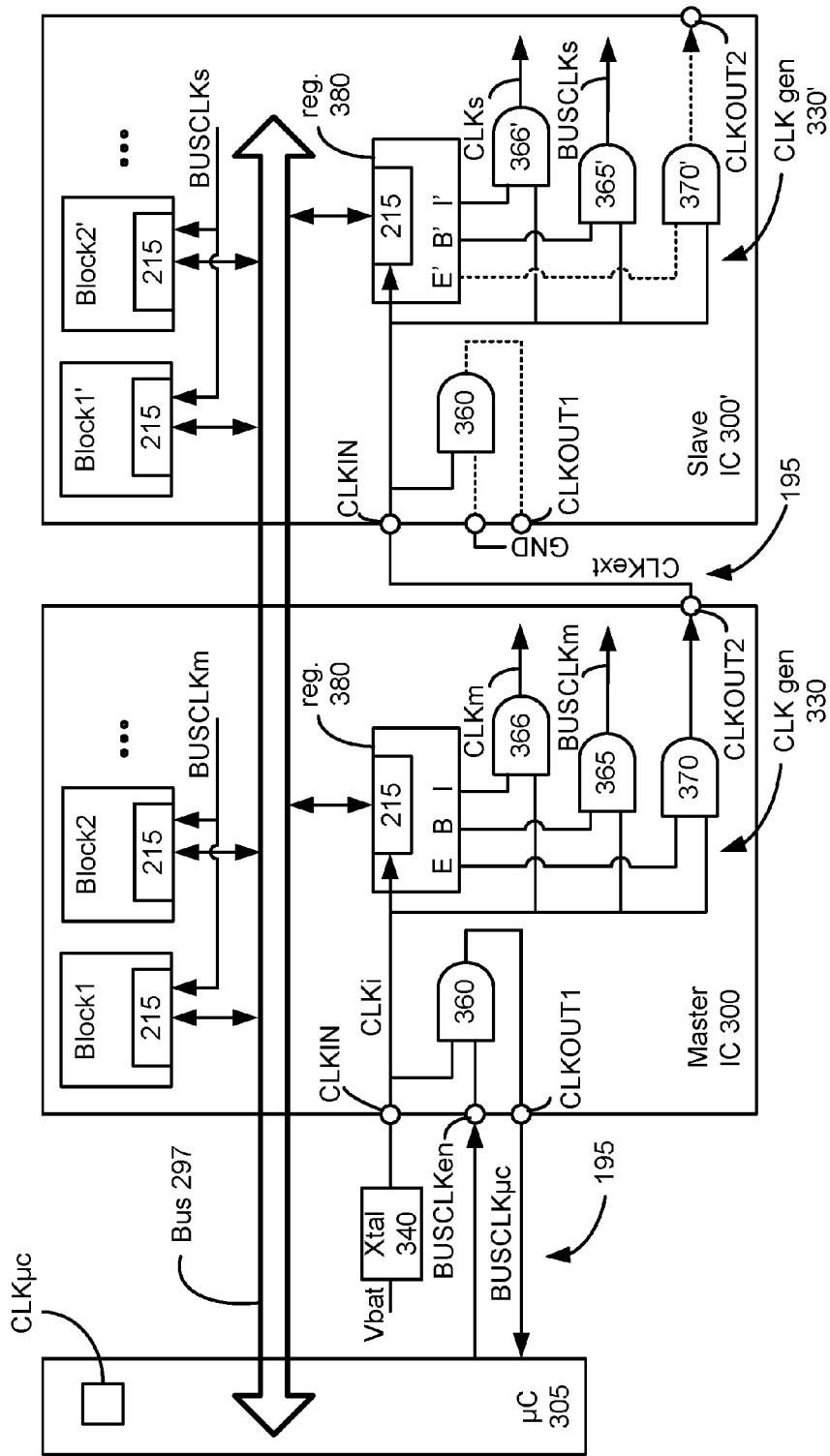
FIG. 10 illustrates aspects of the improved architecture relating to the clocking circuitry, and shows circuitry for disabling clocking at the slave IC as a power saving measure.

Another significant issue addressed by improved system 290 involves clocking, the details of which are shown in FIG. 10. Each of the devices (the microcontroller 305, the master IC 300, and the slave IC 300') requires clocks to function. Each requires clocks to run their internal functions ("internal clocks"), as well as clocks to communicate on the bus 297 ("bus clocks") according to the protocol described earlier (see FIG. 3B). For communications on the bus 297 to be orderly, the bus clocks should be synchronized at each of the devices.

However, there may be times during operation of system 290 when certain internal or bus clocks are not needed. For example, when either the master IC 300 or slave IC 300' are performing an internal operation (e.g., providing stimulation) not requiring bus communications, bus clocking is not required, and only the devices' internal clocks need to be active. In another example, there may be periods of time when only the master IC 300 needs to be clocked. Consider the use of the system 290 when only electrodes on the master IC 300 (E1-E16) are required for patient therapy. During such periods of time, the slave IC 300' may not need to be clocked at all, as that device will neither need to communicate on the bus 297 nor perform any internal operations. In short, not all of the devices in the system 290 will require their internal or bus clocks to be active at a given time. When a particular clock is not required, it is desirable to disable it: significant power can only be drawn during clock transitions, and so shutting down unnecessary clocks in the system save powers, which power is usually limited by the capacity of the battery 26 (FIG. 4B). The disclosed system therefore uses discrete bus and internal clocks in the system, which clocks can be selectively enabled or disabled as needed. Because independent control of particular clocks is desired, a master clock signal is not distributed by the bus 297, as will be made clear below.

FIG. 10 shows the various internal and bus clocks. Microcontroller 305 uses clock signal BUSCLKµc to communicate on the bus 297, and uses clock CLKµc as its internal clock. As noted earlier, the bus protocol can operate relatively slowly, and so BUSCLKµc can be relatively slow, e.g., on the order of 100 kHz. By comparison, the internal clock signal CLKµc that runs the internal functions of the microcontroller 305 can be relatively fast, on the order of several MHz or more, or even GHzs if modern day processors are used.

Master IC 300 uses clock signal BUSCLKm to communicate on the bus 297, and uses clock signal CLKm as its internal clock. Likewise, slave IC 300' uses clock signal BUSCLKs to communicate on the bus 297, and uses clock signal CLKs as its internal clock. As shown, each of the bus clocks BUSCLKm and BUSCLKs are provided to the various functional blocks (Block1, Block 2) in their respective ICs, and more specifically to the bus interface circuitry 215 of such blocks. These functional blocks can comprise any of the functional blocks described earlier with respect to FIG. 4B. The internal clocks CLKm and CLKs are used by the ICs to run internal functions. Although not shown, one important use for internal clocks is to provide reference clocking for the provision of stimulation to the electrodes, which can occur independently of bus communications (or more accurately, after bus communications have already provided the stimulation parameters).

FIG. 10 further illustrates how these various clocks are generated in the system 290, and specially shows the clock generation circuitry blocks 330 and 330' operating in the master and slave ICs 300 and 300' respectively. Communication on the bus 297 is controlled by microcontroller 305, which issues a control signal, BUSCLKen, when communications on the bus 297 are required, i.e., when the microcontroller 305 needs to send or receive data to or from either of the master or slave ICs 300 or 300'. This control signal BUSCLKen is sent to the corresponding input of the master IC 300, but not to the corresponding input of the slave IC 300' by virtue of off-chip routing as shown in FIGS. 4A and 10.

Also received at the master IC 300 at input CLKIN (but not at the slave IC 300') is an initial clock signal, CLKi, generated off chip by a crystal oscillator 340. As will be seen, all of the internal and bus clock signals (expect for the microcontroller's internal clock CLKµc) are generated from (and hence synchronized with) CLKi. It is assumed in FIG. 10 that CLKi from the crystal oscillator 340 is of a proper frequency, which again may be on the order of 100 kHz. However, the signal from the crystal oscillator 340 may also be processed or buffered within the clock generator circuitry 330 to achieve an appropriate clock CLKi (not shown). Although use of a crystal oscillator 340 is shown, other types of clocking circuitries (e.g., ring oscillators) could also be used. Moreover, although CLKi is shown in FIG. 10 as generated off-chip, an on-chip clock generator could also be used. In this case, the M/S controllers 350 and 350' could be used to enable the on-chip clock generator in the master IC 300, but to disable that same generator in the slave IC 300'. CLKi is generally always running, provided the battery 26 in the IPG has not depleted.

CLKi is ANDed with control signal BUSCLKen at AND gate 360 to produce the communication clock BUSCLKµC for the microcontroller 305 at output CLKOUT1. This results in BUSCLKμC being active (and synchronized with CLKi) when BUSCLKen is asserted, and grounded when BUSCLKen is not asserted. Note that the corresponding input for BUSCLKen is grounded in the slave IC 300', which grounds the output to AND gate 360', inactivating output CLKOUT1 on the slave, as represented by the dotted lines.

Once BUSCLKμC is active and the microcontroller 305 can communicate on the bus 297, the microcontroller 305, acting as the system master, can assess which clocks in the master and slave ICs 300 and 300' need to be enabled. Depending on that assessment, the microcontroller 305 can write via the bus 297 to registers 380 and 380' in the master and slave respectively. Specifically shown are three register bits, E, B, and I, which stand for "external," "bus," and "internal." B and B' comprise enable signals for generation of the bus clocks BUSCLKm and BUSCLKs respectively. I and I' comprise enable signals for generation of the internal clocks CLKm and CLKs respectively. (Each of the master and slave can have more than one internal clock, and hence more than one internal clock register value, but only one such clock in shown in FIG. 10 for simplicity). E comprises an enable signal for porting a clock external to the IC 300 (CLKext) to a downstream slave IC such as 300'. Register values E, B, and I are each accessible at their own addresses (e.g., ADDRx, ADDRy, and ADDRz), and each of these addresses can be selectively written to by the microcontroller 305 using the chip select signals CS_m and CS_s discussed earlier.

Starting with the master IC 300, notice that the bus interface circuitry 215 receives the initial clock, CLKi. Because the microcontroller 305's bus clock BUSCLKμc is synchronous with CLKi, this enables register values E, B, and I in register 380 to be set by the microcontroller 305 even though the microcontroller has not yet enabled the remainder of the master IC 300 to fully communicate on the bus 297. Should master IC 300 require its bus clock BUSCLKm to communicate with the microcontroller 305, register value B would be set high by the microcontroller 305. Should master IC 300 require its internal clock CLKm, register value I would be set. When not needed, these registers would be set low. Such register values may default to a high state upon initialization. Like BUSCLKμc, BUSCLKm and CLKm are generated from CLKi using AND gates 365 and 366 respectively, with register values B and I enabling those clocks. As noted earlier, BUSCLKm is sent to the interface circuitry 215 in all other functional blocks within the master IC 300, thus enabling full communication between the microcontroller 305 and all functions in the master IC 300 when BUSCLKm is enabled.

It should be noted that registers B and I are not strictly required in the master IC 300 in all useful embodiments of system 297. Instead, the initial clock signal CLKi can be used directly as the master bus clock BUSCLKm and as the master internal clock CLKm. However, doing so would however prevent the microcontroller 305 from selectively disabling those clock signals at useful times during operation of the system.

The slave IC 300' only receives a clock issued by the master IC 300, namely clock signal CLKext. This occurs when the microcontroller 305 sets the external register E in the master IC 300. Like BUSCLKμc, BUSCLKm, and CLKm, CLKext is formed by ANDing an enable signal (in this case, E) with CLKi, and therefore CLKext is synchronized with all of these other clocks. As shown in FIG. 10, CLKext is output from the master IC 300 and is received at the slave IC 300' at the CLKIN input in the master, effectively taking CLKi's place in the slave. If operation of the slave IC 300' is not required—if slave IC 300' require neither a bus nor internal clock—E is set low, which will ground CLKext and disable the clock signal to the slave IC 300'. Without receipt of a clock signal, the slave IC 300' will draw only nominal power.

If the slave IC 300' is to be operational, E is set high at the master IC 300 and CLKext is enabled. Thereafter, the microcontroller 305 can set the various registers B' and I' in the slave IC 300' depending on whether a bus clock (BUSCLKs) and/or internal clock (CLKs) is required at a given point in time. (Corresponding register E' in the slave IC 300' is irrelevant in the embodiment shown, as the system 290 contains no further downstream slave ICs. As such, the effect of register E' in the slave IC 300' has been depicted with dotted lines). Writing to registers B' and I' occurs at the same addressees (ADDRy and ADDRz) as registers B and I in the master, but with CS_s=1. The status of B' and I' respectively determine whether clocks BUSCLKs and CLKs are enabled, and in the slave these enable signals are ANDed with CLKext at AND gates 365' and 366' respectively. BUSCLKs is sent to the interface circuitry 215 in all other functional blocks within the slave IC 300'. However, this does not necessarily mean that all circuit blocks in the slave will be operative, or that full communications with the slave IC 300' can be had. By way of review, certain circuit blocks in the slave IC 300' will have their interface circuitry 215 disabled by the M/S controller 350' (see FIG. 4C), and thus will be unable to communicate on the bus 297, despite receipt of BUSCLKs.

Because CLKext is ultimately derived from CLKi in the master, clocks BUSCLKs and CLKs are also synchronized with CLKi. To summarize, all of clocks BUSCLKμc, BUSCLKm, BUSCLKs, CLKm and CLKs are synchronized with CLKi, and all will have the same frequency (again, about 100 kHz). Any small delays between these clocks caused by routing or gating are irrelevant given the relatively low operating speed of CLKi. Synchronization is particularly important as concerns the bus clocks, which need to be synchronized for reliable communications on the bus 297. However, synchronization of the internal clocks is important as well to ensure synchronicity in the internal operations between the master and slave, such as during the provision of a stimulation pulse.

It should be noted again that registers B' and I' are not strictly required in the slave IC 300' in all useful embodiments of system 297. Instead, the external clock signal CLKext can be used directly as the slave bus clock BUSCLKs and as the slave internal clock CLKs. However, doing so would however prevent the microcontroller 305 from selectively disabling those clock signals at useful times during operation of the system.

To summarize, by setting register values E, B, I, B', and I', the microcontroller 305 can selectively control the various bus and internal clocks signals needed by the master and slave IC 300'. Importantly, at periods in time when the slave IC 300' is not needed by the system, its clocks can be completely disabled (by setting E low in the master), or partially (by setting E high in the master, but by setting either or both of B' and I' low).

Although FIG. 10 depicts only a single master and slave IC, note that the technique is extendible to control the clock of additional downstream slave ICs.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device, comprising:
   a first integrated circuit comprising a plurality of first electrodes coupleable to a patient's tissue via at least one lead; and
   a second integrated circuit comprising a plurality of second electrodes coupleable to the patient's tissue via the at least one lead,
   wherein the second integrated circuit comprises measurement circuitry configured to receive at least one voltage from any of the first electrodes and configured to receive at least one voltage from any of the second electrodes.

2. The device of claim 1, further comprising at least one connection configured to route the at least one voltage from any of the first electrodes to the second integrated circuit.

3. The device of claim 1, wherein the measurement circuitry is configured to receive a first voltage and a second voltage, wherein the first voltage is selected from any of the first electrodes, and wherein the second voltage is selected from any of the second electrodes.

4. The device of claim 3, wherein the first and second voltages are impressed across holding circuitry in the measurement circuitry.

5. The device of claim 4, wherein the holding circuitry comprises at least one capacitor.

6. The device of claim 3, wherein the measurement circuitry comprises an amplifier for outputting a difference between the first and second voltages.

7. The device of claim 3, wherein the first voltage is selected from a first electrode comprising an anode, and wherein the second voltage is selected from a second electrode comprising a cathode.

8. The device of claim 3, wherein the first voltage is selected from a first electrode comprising an anode, and wherein the second voltage is selected from a second electrode comprising a cathode.

9. The device of claim 1, wherein the measurement circuitry is further configured to receive at least one DC voltage.

10. The device of claim 9, wherein the at least one DC voltage comprises a ground voltage, a voltage of a battery in the device, or a compliance voltage for powering stimulation circuitry in the device.

11. The device of claim 1, wherein the first and second integrated circuits are identical in fabrication.

12. An implantable stimulator device, comprising:
    a first integrated circuit comprising a plurality of first electrodes coupleable to a patient's tissue via at least one lead; and
    a second integrated circuit comprising a plurality of second electrodes coupleable to the patient's tissue via the at least one lead,
    wherein the second integrated circuit comprises measurement circuitry configured to receive at least one voltage from any of the first electrodes.

13. The device of claim 12, further comprising at least one connection configured to route the at least one voltage from any of the first electrodes to the second integrated circuit.

14. The device of claim 12, wherein the measurement circuitry is configured to receive a first voltage and a second voltage selected from any of the first electrodes.

15. The device of claim 14, wherein the first and second voltages are impressed across holding circuitry in the measurement circuitry.

16. The device of claim 15, wherein the holding circuitry comprises at least one capacitor.

17. The device of claim 14, wherein the measurement circuitry comprises an amplifier for outputting a difference between the first and second voltages.

18. The device of claim 14, wherein the first voltage is selected from a first electrode comprising an anode, and wherein the second voltage is selected from a first electrode comprising a cathode.

19. The device of claim 12, wherein the measurement circuitry is further configured to receive at least one DC voltage.

20. The device of claim 19, wherein the at least one DC voltage comprises a ground voltage, a voltage of a battery in the device, or a compliance voltage for powering stimulation circuitry in the device.

21. The device of claim 12, wherein the first and second integrated circuits are identical in fabrication.

* * * * *